United States Patent [19]
Behnke

[11] 4,217,896
[45] Aug. 19, 1980

[54] SYRINGE PLUNGER SNAP-ON PULL RING

[76] Inventor: Robert C. Behnke, Oshkosh, Wis.

[21] Appl. No.: 970,858

[22] Filed: Dec. 19, 1978

[51] Int. Cl.$^2$ ............................................. A61M 5/00
[52] U.S. Cl. ............................................. 128/218 PA
[58] Field of Search ............ 128/218 R, 218 PA, 234, 128/215, 216, 213

[56] References Cited

U.S. PATENT DOCUMENTS

| | | | |
|---|---|---|---|
| 1,798,116 | 3/1931 | Brockway | 128/218 PA |
| 2,823,675 | 2/1958 | Sciurba | 128/218 PA |
| 2,842,128 | 7/1958 | Hein, Jr. | 128/218 PA |

FOREIGN PATENT DOCUMENTS 795202  5/1958  United Kingdom ............ 128/218 PA

*Primary Examiner*—John D. Yasko
*Attorney, Agent, or Firm*—Clarence A. O'Brien; Harvey B. Jacobson

[57] ABSTRACT

A ring-type body is provided comprising a plurality of closed continuous convolutions of wire and one end portion of the wire, of an angular extent somewhat less than 360 degrees, includes a slightly greater radius of curvature whereby it is spaced outwardly of the adjacent convolutions. The end portion terminates in a smoothly curved back turned portion defining a U-shaped seat structure for embracingly receiving the free end portion of the plunger of a syringe structure immediately inwardly of the diametrically enlarged terminal end flange thereof, the flange of the syringe plunger being clamped between the U-shaped seat structure and the opposing outer surface portions of the adjacent convolutions. The entire ring-type body including the integral wire portion defining the aforementioned U-shaped seat is constructed from a single length of wire material.

7 Claims, 7 Drawing Figures

U.S. Patent   Aug. 19, 1980   4,217,896
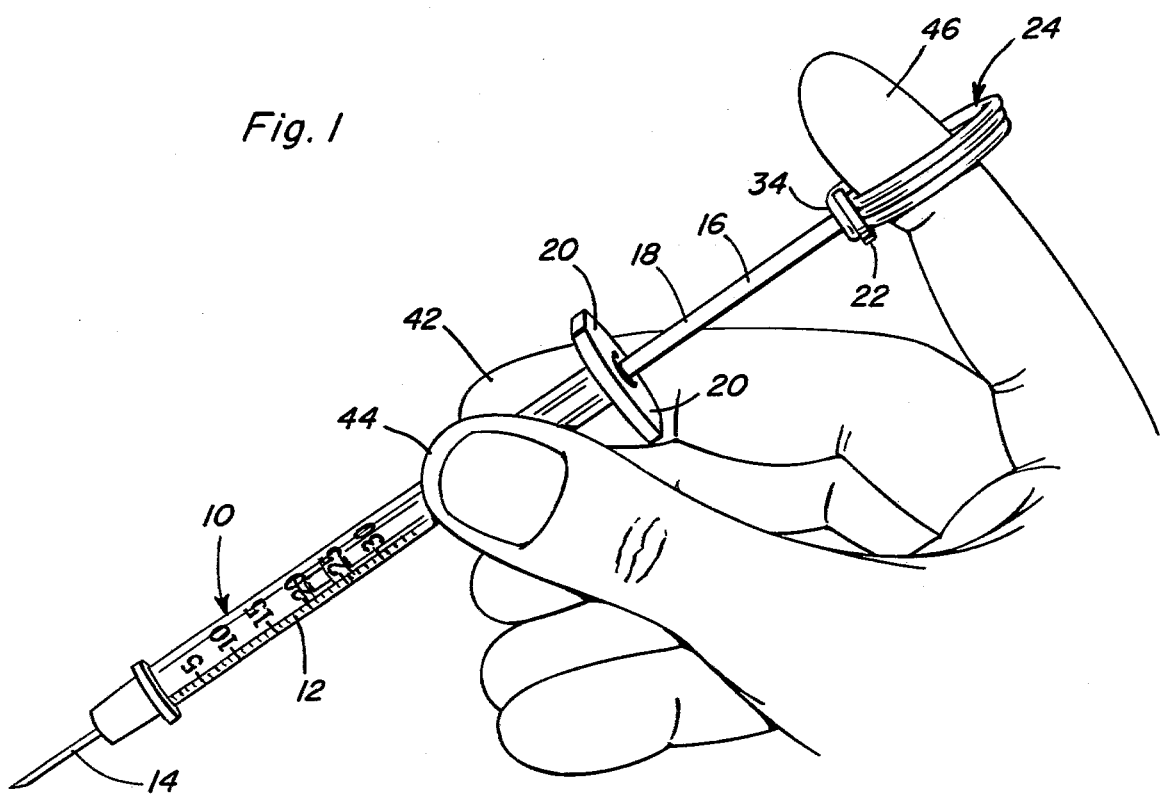
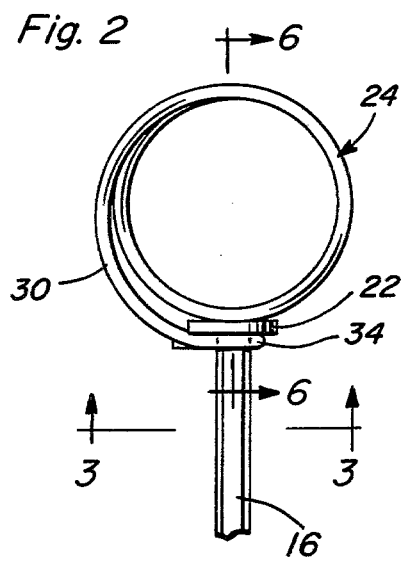
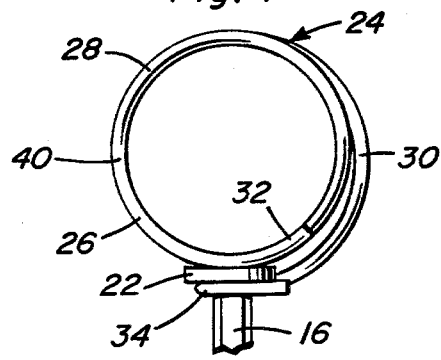
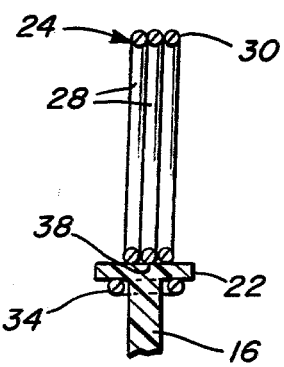
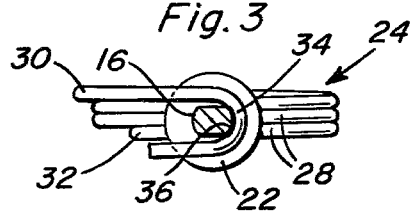
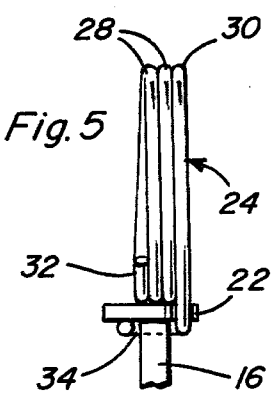
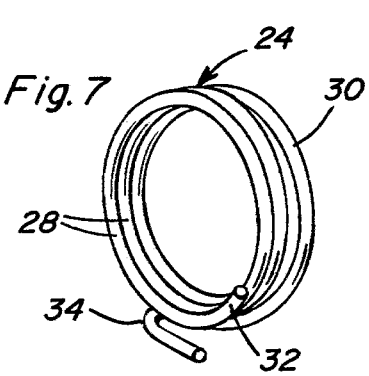

SYRINGE PLUNGER SNAP-ON PULL RING

BACKGROUND OF THE INVENTION

Various persons, and particularly those requiring insulin, must inject themselves with medication. While conventional syringe structures are readily usable with both hands, they are not readily usable by only one hand and, accordingly, a person wishing to inject himself with insulin in an arm location has difficulty in manipulating the syringe effectively. Accordingly, a need exists for a type of syringe which may be effectively supported in correct position and actuated to complete an injection while using only one hand.

Although some forms of syringe assemblies have heretofore been provided with permanent finger engageable ring portions supported from the plungers thereof, with the recent wide spread use of "throw-away38 type syringes, the additional cost of constructing a syringe including a finger ring on the plunger portion thereof has made the inclusion of such a finger-ring on a "throw-away" syringe assembly cost prohibitive.

Although some forms of removable finger rings have been also heretofore provided for use on the plunger portions of syringe assemblies, these removable finger rings either relatively expensive, time consuming in installation or unable to maintain a firm connection between the ring and the associated syringe plunger.

Examples of syringe plunger rings including some of the general structural and operational features of the instant invention are disclosed in U.S. Pat. Nos. 822,079, 1,798,116, 2,823,675, and 2,842,128.

BRIEF DESCRIPTION OF THE INVENTION

The ring of the instant invention is constructed of a single length of stiff wire and is formed into a plurality of a side-by-side convolutions of substantially the same diameter. However, one end portion of the wire is of a radius of curvature somewhat greater than the remaining convolutions thereof and terminates in a back turned portion defining a U-shaped seat overlying the adjacent smaller radius of curvature convolutions. The end flange on the plunger of a syringe assembly may be clampingly received between the back turned U-shaped seat defining terminal end of the wire and the opposing peripheral portions of the smaller diameter wire convolutions with the end of the plunger adjacent the terminal end flange seated in the U-shaped seat.

The main object of this invention is to provide a finger ring which may be readily removably clamping engaged with the diametrically enlarged terminal end flange on the plunger portion of a syringe assembly in a manner such that the ring is supported from the plunger portion in a manner against accidental dislodgment therefrom.

Another object of this invention is to provide a finger engageable ring in accordance with the proceding objects and which may be readily removably supported from an associated syringe plunger.

Still another object of this invention is to provide a finger ring which will be adaptable for removable securement to syringe plungers of different manufacture.

A final object of this invention to be specifically enumerated herein is to provide a finger ring in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of a conventional "throw-away" syringe assembly and with the finger engageable pull ring of the instant invention operatively associated with the end flange of the plunger of the syringe assembly;

FIG. 2 is an enlarged fragmentary side elevational view of the terminal end of the syringe plunger illustrating the pull ring operatively associated thereof;

FIG. 3 is a horizontal sectional view taken substantially upon the plane indicated by the section line 3—3 of FIG. 2;

FIG. 4 is a fragmentary elevational view similar to FIG. 2 but illustrating the finger ring and associated plunger portion as seen from the background of FIG. 2;

FIG. 5 is a fragmentary elevational view of the assemblage illustrated in FIG. 4 as seen from the right side thereof;

FIG. 6 is a fragmentary vertical sectional view taken substantially upon the plane indicated by the section line 6—6 of FIG. 2; and FIG. 7 is a perspective view of the pull ring.

DETAILED DESCRIPTION OF THE INVENTION

Referring now more specifically to the drawings, the numeral 10 generally designates a syringe assembly including a tubular barrel portion 12 open at one end and having an injection needle 14 supported from its other end. The open end of the barrel portion 12 has the free end 16 of the plunger portion 18 of the syringe assembly 10 projecting outwardly thereof and further includes diametrically oppositely, outwardly projecting conventional flange portions 20.

The free end 16 of the plunger 18 supports a diametrically enlarged end flange 22 therefrom and the pull ring of the instant invention is referred to in general by the reference numeral 24 and is supportingly clampingly engaged with the end flange 22 and the adjacent portion of the free end 16 of the plunger portion 18.

The pull ring 24 comprises a single piece of wire formed into a plurality of convolutions 28 of the same diameter and a further convolution 30 of somewhat less than 360 degrees angular extent and having a slightly greater radius of curvature than the convolutions 28. The free end of the convolution 30 overlaps, peripherally about the body 26, the free end 32 of the convolution 28 remote from the convolution 30 and the free end of the convolution 30 terminates in a smoothly curved back turned portion 34 defining a U-shaped seat 36.

The greater radius of curvature of the convolution 30 spaces the back turned portion 34 defining the seat 36 slightly outwardly of the outer periphery of the convolutions 28. Those outer surface portions of the convolutions 28 opposing the back turned portion 34 define abutment surface means 38 facing generally outwardly of the ring body 26 and disposed in a plane generally paralleling the center axis of the ring and tangential to the outer surface of the ring at the abutment surface means 38. The back turned portion 34 is spaced on the side of the aforementioned plane remote from the abutment surface means 38 and the wire 40 of which the body 26 is constructed is stiff and sufficiently resilient to support the U-shaped back turned portion 34 from the convolution 28 of the body 26 in position spaced from the abutment surface means 38 and in a manner yieldingly resisting movement of the back turned portion 34 outwardly away from the abutment surface means 38.

Thus, the free end 16 of the plunger portion 18 may be seatingly engaged within the seat 36 with the flange 22 clamped between the abutment surface means 38 and those surface portions of the back turned portion 34 opposing the abutment surface means 38. In this manner, the pull ring 24 is removably supported from the plunger portion 18 against accidental dislodgment therefrom.

From FIG. 1 of the drawings it may be seen that the barrel portion 12 of the syringe assembly 10 may be held between the second finger 42 and thumb 44 of the user while the forefinger 46 of the user is inserted through the pull ring 24. In this manner, the pull ring 24 may be utilized to withdraw the plunger portion 18 from the barrel portion 12 or to telescope the plunger portion 18 into the barrel portion 12.

When the syringe assembly 10 is held in the manner illustrated in FIG. 1 of the drawings, the user may readily inject himself with the prescribed medication in any location which is accessible to the single hand by which he is supporting the syringe assembly 10.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A syringe plunger pull ring for ready attachment to the enlarged end flange of the exposed end of the plunger of a hypodermic syringe assembly, said pull ring including a peripherally continuous ring-shaped body for receiving a finger therethrough and defining, at least at one location thereof about its periphery, abutment surface means facing generally radially outwardly of the body and disposed in a plane generally paralleling the center axis of the body and tangential to the outer surface of the body at said one location thereon, said body further including structure defining a generally U-shaped retainer portion substantially paralleling said plane, spaced slightly outward from said body on the side of said plane remote from said body and resiliently supported from said body to yieldingly resist displacement further away from said abutment surface means, said U-shaped retainer portion opening in a direction substantially paralleling a plane containing said body, the spacing between said retainer portion and said abutment surface means being slightly less than the thickness, measured in the direction of the longitudinal extent of the plunger, of end flange, and said U-shaped retainer portion being adapted to seatingly receive said plunger, inwardly of said end flange, therein.

2. The combination of claim 1 wherein said body comprises a plurality of coextensive side-by-side complete convolutions of a length of wire.

3. The combination of claim 2 wherein said U-shaped retainer portion is supported from one end portion of said wire.

4. The combination of claim 3 wherein said retainer portion comprises an integral smoothly back turned portion of said one end portion of said wire.

5. The combination of claim 4 wherein said one end portion of said wire extends about said body an angular extent less than 360 degrees and is of a radius of curvature slightly greater than the radius of curvature of said convolutions of said wire, whereby said retainer portion carried by said one end of said wire is spaced slightly outwardly of the adjacent abutment surface means defining portions of said convolutions.

6. The combination of claim 5 wherein said body includes two adjacent convolutions of said wire and said wire end portion of the greater radius of curvature, said wire end portion peripherally overlapping the terminal end of the remote convolution of said wire.

7. A syringe plunger pull ring for ready attachment to the enlarged end flange of the exposed end of the plunger of a hypodermic syringe assembly, said pull ring including a peripherally continuous ring-shaped body for receiving a finger therethrough and defining, at least at one location thereof about its periphery, abutment surface means facing generally radially outwardly of the body and disposed in a plane generally paralleling the center axis of the body and tangential to the outer surface of the body at said one location thereon, said body further including seat structure spaced slightly radially outwardly of said abutment surface means, said seat structure defining a U-shaped notch opening in a direction paralleling said plane and paralleling the adjacent peripheral portion of said body, said seat structure being resiliently supported from said body for yieldingly resisting displacement of said seat structure away from said abutment surface means of said body, the spacing between said seat structure and said abutment surface means being slightly less than the thickness, measured in the direction of the longitudinal extent of said plunger, of said flange, and said seat structure being adapted to seatingly receive said plunger, inwardly of said end flange, therein.

* * * * *